US011821040B2

(12) United States Patent
Rurup et al.

(10) Patent No.: US 11,821,040 B2
(45) Date of Patent: Nov. 21, 2023

(54) DETECTION OF CANCER IN URINE

(71) Applicant: NANOMED DIAGNOSTICS B.V., Enschede (NL)

(72) Inventors: Willem Frederik Rurup, Best (NL); Loes Irene Segerink, Enschede (NL); Roderik Adriaan Kraaijenhagen, Amstelveen (NL); Herbert Michael Pinedo, Amsterdam (NL); Albert Van Den Berg, Nijverdal (NL); Renske Daniëla Maria Steenbergen, Enschede (NL); Jacobus Adrianus Nieuwenhuijzen, Amsterdam (NL); Idris Bahce, Enschede (NL); Geert Kazemier, Enschede (NL)

(73) Assignee: Nanomed Diagnostics BV, Enschede (NL)

( * ) Notice: Subject to any disclaimer, the term of this patent is extended or adjusted under 35 U.S.C. 154(b) by 135 days.

(21) Appl. No.: 16/089,222

(22) PCT Filed: Mar. 31, 2017

(86) PCT No.: PCT/NL2017/050199
§ 371 (c)(1),
(2) Date: Sep. 27, 2018

(87) PCT Pub. No.: WO2017/171548
PCT Pub. Date: Oct. 5, 2017

(65) Prior Publication Data
US 2019/0241963 A1  Aug. 8, 2019

(30) Foreign Application Priority Data
Apr. 1, 2016  (EP) ..................... 16163585

(51) Int. Cl.
*C12Q 1/6886* (2018.01)
*C12Q 1/6806* (2018.01)
*C12Q 1/686* (2018.01)

(52) U.S. Cl.
CPC ......... *C12Q 1/6886* (2013.01); *C12Q 1/6806* (2013.01); *C12Q 1/686* (2013.01); *C12Q 2600/112* (2013.01); *C12Q 2600/118* (2013.01); *C12Q 2600/154* (2013.01); *C12Q 2600/156* (2013.01); *C12Q 2600/16* (2013.01)

(58) Field of Classification Search
CPC .............................. C12Q 1/6886; C12Q 1/686
See application file for complete search history.

(56) References Cited

U.S. PATENT DOCUMENTS

| 8,399,193 | B2 | 3/2013 | Pfeifer et al. | |
|---|---|---|---|---|
| 2010/0143899 | A1* | 6/2010 | Bosenberg | C12Q 1/6886 |
| | | | | 435/6.14 |
| 2011/0027796 | A1 | 2/2011 | An et al. | |
| 2011/0117551 | A1* | 5/2011 | Van Criekinge | C12Q 1/6886 |
| | | | | 435/6.14 |
| 2013/0210011 | A1* | 8/2013 | Lind | C12Q 1/6886 |
| | | | | 435/6.11 |
| 2014/0155279 | A1* | 6/2014 | Song | C12Q 1/6886 |
| | | | | 435/6.12 |
| 2014/0271455 | A1 | 9/2014 | Pfeifer et al. | |
| 2017/0058356 | A1* | 3/2017 | Ahlquist | C12Q 1/6886 |

FOREIGN PATENT DOCUMENTS

| CN | 102399860 A | 4/2012 |
|---|---|---|
| CN | 104232763 A | 12/2014 |
| JP | 2015177745 A | 10/2015 |
| WO | WO2008155549 A2 | 12/2008 |
| WO | 2009036922 A2 | 3/2009 |
| WO | WO2009069984 A2 | 6/2009 |
| WO | 2009113771 A1 | 9/2009 |
| WO | WO2014183093 A1 | 11/2014 |

OTHER PUBLICATIONS

Renard, Identification and Validation of the Methylated TWIST1 and NID2 Genes through Real-Time Methylation-Specific Polymerase Chain Reaction Assays for the Noninvasive Detection of Primary Bladder Cancer in Urine Samples, Eur. Urol., 58: 96-104, 2010. (Year: 2010).*
Feng, Promoter Hypermethylation of Tumor Suppressor Genes in Urine from Patients with Cervical Neoplasia, Cancer Epidemiol Biomarkers Prev, 16(6): 1178-1184, 2007. (Year: 2007).*
Grote, Methylation of RAS Association Domain Family Protein 1A as a Biomarker of Lung Cancer, Cancer Cytopathology, 108(2): 129-134, 2006. (Year: 2006).*
Lee, Methylation of TMEFF2 gene in tissue and serum DNA from patients with non-small cell lung cancer, Mol Cells., 34(2): 171-176, 2012. (Year: 2012).*
Costa, Three epigenetic biomarkers, GDF15, TMEFFs, and VIM, accurately predict bladder cancer from DNA-based analyses of urine samples, Clin Cancer Res., 16(23): 5842-5951, 2010. (Year: 2010).*

(Continued)

*Primary Examiner* — Angela M. Bertagna
*Assistant Examiner* — Carolyn L Greene
(74) *Attorney, Agent, or Firm* — Patent Law Works LLP

(57) ABSTRACT

The invention provides in vitro methods of determining whether an individual has a pre-cancer or cancer comprising determining the presence or absence of one or more methylation markers of a methylation marker set in a urine sample of said individual; and determining whether the individual has pre-cancer or cancer based on the detection of the presence or absence of said one or more methylation markers in the urine sample, wherein the presence of said one or more methylation markers indicates that the individual has pre-cancer or cancer. The invention further provides methods for typing pre-cancer or cancer based on the the presence or absence of one or more methylation markers of a methylation marker set in a urine sample.

6 Claims, 2 Drawing Sheets
Specification includes a Sequence Listing.

(56) References Cited

OTHER PUBLICATIONS

Tessema, GATA2 is epigenetically repressed in human and mouse lung tumors and is not requisite for survival of KRAS mutant lung cancer, J Thorac Oncol., 9(6): 784-793, 2014. (Year: 2014).*

Kandimalla, Genome-wide Analysis of CpG Island Methylation in Bladder Cancer Identified TBX2, TBX3, GATA2, and ZIC4 as pTa-Specific Prognostic Markers, Urothelial Cancer, 61(6): 1245-1256, 2012. (Year: 2012).*

Shivapurkar, Cytoglobin, the Newest Member of the Globin Family, Functions as a Tumor Suppressor Gene, Cancer Res., 68(18): 7448-7456, 2008. (Year: 2008).*

Andersson, et al., "Filtration Device for On-Site Collection, Storage and Shipment of Cells from Urine and Its Application to Dna-Based Detection of Bladder Cancer." Plos One. 10.7 (2015). XP 055300496, DOI:http://dx.doi.org/10.1371/journal.pone.0131889.

Jain, et al. 2015. "Differential methylation of the promoter and first exon of the RASSF1A gene in hepatocarcinogenesis". Hepatology Research : the Official Journal of the Japan Society of Hepatology. 45 (11): 1110-23. XP 055300588, DOI:http://dx.doi.org/10.1111/hepr.12449.

PCT International Search Report and Written Opinion, Application No. PCT/NL2017/050199, dated Jun. 22, 2017.

Reinert, et al., "Diagnosis of Bladder Cancer Recurrence Based on Urinary Levels of Eomes, Hoxa9, Pou4f2, Twist1, Vim, and Znf154 Hypermethylation." Plos One. 7.10 (2012) XP 055295205, DOI:http://dx.doi.org/10.1371/journal.pone.0046297.

EPO Communicatio Pursuant to Article 94(3) EPC, European Patent Office, dated Feb. 6, 2020, Application No. 17718146.8 NanoMedDiagnostics B.V., 11 pages.

Marshall, Fray F. "Quantitative Detection of Promoter Hypermethylation of Multiple Genes in the Tumor, Urine, and Serum DNA of Patients With Renal Cancer." The Journal of Urology, Lippincott Williams Wilkins, Baltimore, MD, US, vol. 193, No. 4, Jun. 2005, p. 1918, ISSN: 0022-5347.

Wahab, Abdel Hady Abdel, el al. "Promoter Hypermethylation of RASSF1A, MGMT, and HIC-1 Genes in Benign and Malignant Colorectal Tumors." Tumor Biology: Tumor Markers, Tumor Targeting and Translational Cancer Research, vol. 32, No. 5, 2011, p. 845. EBSCOhost, doi:10.1007/s13277-011-0155-7.

Xiong, Gengyan, et al. "Mp2-03 Prognostic and Predictive Value of Epigenetic Biomarkers in Upper Tract Urothelial Carcinoma." The Journal of Urology, vol. 193, No. 4, Apr. 2015, p. e11. EBSCOhost, doi:10.1016/j.juro.2015.02.126.

Feng, Hongxiang, et al. "Promoter Methylation of APC and RAR-b Genes as Prognostic Markers in Non-Small Cell Lung Cancer (NSCLC)." Experimental and Molecular Pathology, vol. 100, No. 1, 2016, pp. 109-113.

Wang, Yucai, et al. "Identification of Epigenetic Aberrant Promoter Methylation of RASSF1A in Serum DNA and Its Clinicopathological Significance in Lung Cancer." Lung Cancer (Amsterdam, Netherlands), vol. 56, No. 2, 2006, pp. 289-294.

* cited by examiner

DETECTION OF CANCER IN URINE

The invention relates to the field of analyzing urine samples. In particular the invention relates to the identification of cancerous nucleic acid in the urine of individuals, in particular methylated nucleic acid.

Cancer is nearly always diagnosed by an expert who has looked at cell or tissue samples under a microscope. In some cases, tests done on the cells' proteins, DNA, and RNA can help tell doctors if there is cancer. These test results are important when choosing the best treatment options.

Such tests are typically performed when an individual registers itself with complaints. In such cases, if it is cancer, chances are that the cancer has already progressed to such an extent that simple surgery is not curative or the chance of metastasis is significant resulting in a need for invasive treatments with chemotherapy and/or radiation and a poor general prognosis.

On the other hand, when the complaints are not caused by cancer the patient is left in uncertainty for a considerable amount of time waiting for the results of the biopsy.

There is thus a need for a simple, quick and non-invasive method to determine whether the individual has cancer and, if it is cancer, what type of cancer it is.

The present invention provides means and methods for the detection and the typing of cancer and pre-cancer in urine samples. The means and methods detects nucleic acid, and in particular DNA in the urine and detects and types cancer or pre-cancer by analyzing the methylation state of the detected nucleic acid.

It is known in the art that certain types of cancer and pre-cancer are associated with the methylation of certain genes. Methylation of DNA is a natural process and typically occurs when cells differentiate to specialized cells in the body. DNA methylation is a process by which methyl groups are added to DNA. Methylation has been shown to alter the behavior and the function of certain DNAs. When located in a gene promoter, DNA methylation typically acts to repress gene transcription. DNA methylation is essential for normal development and is associated with a number of key processes including genomic imprinting, X-chromosome inactivation, repression of repetitive elements and ageing. In disease it has been associated with cancer.

In eukaryotes, methylation is restricted to one of the DNA's four nucleotides. The incidence of cytosine DNA methylation differs between species. DNA methylation typically occurs in a CpG dinucleotide context. Other forms of methylation have been detected, mostly in embryonic stem cells or neural development.

Between 60% and 90% of all CpGs are methylated in mammals. Methylated C residues spontaneously deaminate to form T residues over time, which is thought to be the reason for the relative under-representation of CpG dinucleotides in the human genome.

Unmethylated CpGs are often grouped in clusters called CpG islands, which are present in the 5' regulatory regions of many genes. In cancer and pre-cancer, gene promoter CpG islands acquire abnormal hypermethylation, which results in transcriptional silencing that can be inherited by daughter cells following cell division. Alterations of DNA methylation have been recognized as an important component of cancer development. Hypomethylation, in general, arises earlier and is linked to chromosomal instability and loss of imprinting, whereas hypermethylation is associated with promoters.

The glomerular filtration barrier causes substances of low molecular weight (<5500 Da) and small effective molecular radius (e.g., water, urea and glucose) to appear in the filtrate in the same concentration as in plasma. Larger and larger macromolecules are increasingly restricted from passage so that only traces of plasma albumin (69 kDa) are normally present in the glomerular filtrate. Other factors such as the radius and electrical charge also influence the appearance of substances in the filtrate. Measurements suggest that the glomerular filtration restricts the passage of anions but enhances the passage of cations. This conclusion was based in part on the observation that longer and/or more negatively charged sugar-chains (dextrans) appear to pass with lower efficiency.

The function of renal tubules is to recover most of the fluid and solutes filtered at the glomerulus. If the fluid was not recovered, the kidney would excrete the volume of the entire blood plasma in less than half an hour. In the tubules NaCl, $NaHCO_3$, filtered nutrients (e.g., glucose and amino acids), divalent ions (e.g., $Ca^{2+}$, $HPO_4^{2-}$, and $SO_4^{2-}$), and water are reabsorbed. Finally, the proximal tubule secretes $NH_4^+$ and a variety of endogenous and exogenous solutes into the lumen making a concentrate with waste products, to compose the final urine (Boulpaep, et al, Medical Physiology, 2012, Philadelphia: Saunders).

Among the different components of urine it was found that some DNA is also present. The majority of the DNA in urine is found in cells. According to a manufacturer of DNA isolation kits specific for urine (Zymoresearch), the total amount of recoverable DNA is approximately 5-25 µg/L urine.

SUMMARY OF THE INVENTION

The invention provides an in vitro method determining whether an individual detecting has a pre-cancer or cancer comprising
determining the presence or absence of one or more methylation markers of a methylation marker set in a urine sample of said individual; and determining whether the individual has pre-cancer or cancer based on
the detection of the presence of said one or more methylation markers in the urine sample, wherein the presence or absence of said one or more methylation markers indicates that the individual has pre-cancer or cancer and the absence of the methylation markers indicates that the individual does not have pre-cancer or cancer.

The invention also provides an in vitro method of determining a type of pre-cancer or cancer in an individual that has cancer comprising
determining the presence or absence of one or more methylation markers of a methylation marker set in a urine sample of said individual; and
determining pre-cancer or cancer type(s) based on the detection of the presence or absence of said one or more methylation markers in the urine sample, wherein the presence or absence of said one or more methylation markers is indicative for one or more types of pre-cancer or cancer of said individual.

The invention further provides a kit comprising means for the detection of one or more methylation markers in a methylation marker set wherein the set comprises at least one methylation marker selected from the group consisting of the methylation markers identified in Table 9 and wherein the set further comprises an nucleic acid extraction buffer for extraction of nucleic acid from urine.

Also provided is a nucleic acid amplification device comprising at least two nucleic acid amplification primers for amplifying nucleic acid of one or more methylation markers from a methylation marker set.

The invention further provides the use of kit according to the invention or a device according to the invention, for determining the type of pre-cancer or cancer of an individual with cancer from a urine sample of the individual.

The invention further provides the use of kit according to the invention or a device according to the invention, for detecting a pre-cancer or cancer in an individual from a urine sample of the individual.

DETAILED DESCRIPTION OF THE INVENTION

The invention provides in vitro methods of determining whether an individual has a pre-cancer or cancer in an individual. The present invention further provides in vitro methods of determining a type of a pre-cancer or cancer in an individual that has pre-cancer or cancer. The methods comprise determining the presence or absence of one or more methylation markers of a methylation marker set in a urine sample of said individual. Pre-cancer and cancer types can be determined from the detection of the presence or absence of one or more particular methylation markers in the urine of the individual. The presence and/or the absence of certain methylation marker(s) is indicative for a type of pre-cancer or cancer the individual is likely to have. The presence or absence of one or more methylation markers indicates that the individual has pre-cancer or cancer and the absence of the methylation markers indicates that the individual does not have pre-cancer or cancer.

Various pre-cancers and cancers can be detected with the invention. Whereas some methylation markers are always detected, irrespective of the presence or absence of pre-cancer or cancer, some methylation markers are only detected in the urine when the individual has pre-cancer or cancer. Some cancer methylation markers are detected with various types of pre-cancer or cancer and are thus suited for determining whether the individual has pre-cancer or cancer as such, and (when combined with other methylation markers) also for typing cancer.

A precancerous condition or premalignant condition, sometimes called a potentially precancerous condition or potentially premalignant condition, is a state of disordered morphology of cells that is associated with an increased risk of cancer. If left untreated, these conditions may lead to cancer. Such conditions are usually dysplasia or benign neoplasia. Sometimes the term "pre-cancer" is used to describe carcinoma in situ, which is a noninvasive cancer that has not progressed to an aggressive, invasive stage. Not all carcinoma in situ will progress to invasive disease.

Pre-cancer (also referred to as premalignant) lesions are morphologically atypical tissue which appears abnormal under microscopic examination, and in which cancer is more likely to occur than in its apparently normal counterpart. Examples of pre-cancers are actinic keratosis; Barrett's esophagus; atrophic gastritis; dyskeratosis congenital; sideropenic dysphagia; lichen planus; oral submucous fibrosis; solar elastosis; cervical dysplasia; leukoplakia; polyposis coli and erythroplakia. In a preferred embodiment the pre-cancer is polyposis coli. Cancers that can be detected and/or types comprise and preferably consist of lung cancer, preferably non-small cell lung cancer, cervical cancer, prostate cancer, ovarian carcinoma, breast cancer, including ductal carcinoma in situ, head and neck cancer, Urothelial cell carcinoma such as bladder cancer, Hematological malignancies such as but not limited to myeloma, leukemia, lymphoma and myelodysplastic syndrome, a cancer of the gastrointestinal tract (GI tract) and accessory organs of digestion, including but not limited to the esophagus, stomach, biliary system, pancreas, small intestine, large intestine, and rectum. In a preferred embodiment the cancer that is to be detected comprises lung cancer, preferably non-small cell lung cancer, breast cancer, head and neck cancer, Hematological malignancies such as but not limited to myeloma, leukemia, lymphoma and myelodysplastic syndrome, a cancer of GI tract or accessory organs of digestion, including but not limited to the esophagus, stomach, biliary system, pancreas, small intestine, large intestine, rectum, gall bladder, liver and anus. Cancer in the present invention indicates primary cancer and metastasized cancer.

It is preferred that the pre-cancer or cancer is a pre-cancer or cancer of which the nucleic acid has had to pass the kidney to arrive in the urine. Even in a carefully collected urine sample, cancers such as Urothelial cell carcinoma such as bladder cancer or the pre-cancerous precursor stages thereof can shed nucleic acid directly into the urine without having to pass through the kidney. Pre-cancer lesions or cancer can be detected by detecting at least some of the methylation markers associated with urine of individuals in which the pre-cancerous state has progressed to cancer. In a preferred embodiment the cancer is not Urothelial cell carcinoma, cervical cancer or prostate cancer, or a pre-cancer stage thereof. In a preferred embodiment the cancer is not bladder cancer or a pre-cancer stage thereof.

Typing of a pre-cancer or cancer typically involves determining the tissue of origination of the cancer. For instance, bladder cancer that has metastasized to the lung is typically typed as bladder cancer. Typing can include determining whether a cancer is likely to have metastasized, this is optional. The typing can also result in the determination that the individual has one or more of several types of pre-cancer or cancer.

The individual is preferably a mammal, preferably a human.

Urine is a solution of which the concentration of components can vary in response to diet and the amount of liquid consumed. Among the various well known components of urine, nucleic acid is also present. Most of the DNA in urine is found in associated with cells. Commercial sources mention that the amount of DNA that can be recovered from urine is one average about 5-100 jig/L. In the present invention it is preferred that sample is a cell free urine sample. DNA can cross the kidney barrier in a polymer state, with fragments large enough (on average 150 bp) to be amplified with PCR. Cell free DNA in urine is on average about 2-100 jig/L. Not all urine samples contain sufficient DNA for analysis. Such samples are typically identified by performing a control. A suitable control is a PCR to determine the presence of a standard DNA such as actin. In cases of insufficient DNA it is often sufficient to collect a further sample of the individual. Alternatively the DNA can be concentrated from larger volumes of urine. It is also possible to concentrate urine by for example freeze drying.

Male gene fragments were shown in female urine after blood transfusion or in woman pregnant with males. In rodents injected human DNA sequences could also be amplified in the urine. Another study was able to capture 47-65 pg/μL (cell free) DNA per 1 mL sample (equaling 47-65 μg/L). Furthermore, colorectal tumor related mutations have been shown in free DNA derived from urine (Su et al 2008; Ann N Y Acad Sci. 2008 August; 1137: 197-206). Long-term storage of urine can affect the quality of DNA. Thus typically fresh urine samples are used in the present invention, typically samples are used within one day of sample, however, longer waiting times are possible upon appropriate processing of the urine sample (see for instance Hilhorst et al. 2013; BMC Nephrol, 2013. 14: p. 238). Other DNA preservations means and methods are also possible such as, for instance, commercially offered by Zymo research (urine conditioning buffer) which preserves DNA at room temperature for a number of days.

Aberrantly methylated cytosine at CpG dinucleotides is a widespread phenomenon in cancer. (Jones, P A and Laird, P W, "Cancer epigenetics comes of age," Nat. Genet. 21: 163-167 (1999)). As a result of CpG island hypermethylation, chromatin structure in the promoter can be altered, preventing normal interaction with the transcriptional machinery. (Baylin, S B, et al. "Alterations in DNA methylation: A fundamental aspect of neoplasia," Advances in cancer research (eds. G. F. Nande Woude and G. Klein), vol. 72: 141-196 (1998), Academic Press, San Diego, CA). When this occurs in genes that are relevant to growth inhibition, the resulting silencing of transcription could promote tumor progression. In addition, promoter CpG island hypermethylation has been shown to be a common mechanism for transcriptional inactivation of classic tumor suppressor genes and genes important for cell cycle regulation, and DNA mismatch repair. Methylation of cytosine, therefore, plays a significant role in control of gene expression, and a change in the methylation pattern or status is likely to cause disease. Differences in methylation at CpG dinucleotides between a normal state, a pre-cancer state and the cancer state of a cell are herein referred to as methylation markers. The detection of such a methylation marker in urine can be an indication that the individual has pre-cancer or cancer. Chromosomal DNA that has an increased methylation of CpG dinucleotides is also referred to as hypermethylated DNA. Hypermethylation in general is associated with the cancerous or pre-cancerous state of a cell. Methylation markers can be detected in various ways. Detection can be performed by using methylation assays capable of determining differential methylation levels within CpG sites between diseased cells or tissues and normal cells or tissues. Methylation-specific assays useful for this purpose include, for example, methylation-specific PCR, bisulfite genomic sequencing methods, methylation-specific primer extension methods, and other methods known in the art, and with high throughput or microarrays. Suitable methods for the detection of methylation markers are described in Shanmuganathan et al (2013) Journal of Molecular Diagnostics Vol 15: pp 17-26. This reference and the papers referred to therein in as far as they delineate methods for detection of methylation markers are incorporated by reference herein. A suitable method for next-generation bisulphite amplicon sequencing is described in Margolin et al (2016) Vol 18: pp 283-298, which is also incorporated by reference herein. A suitable device is disclosed in WO2009104967 which is also incorporated by reference herein.

Methylation markers of the present invention are typically not detected in the urine of individuals that do not have pre-cancer or cancer. Methylation markers of the present invention are only detected when the individual has pre-cancer or cancer. Different pre-cancers or cancers may be associated with different methylation markers in the urine. Such differences are exploited in the present invention for the typing of a pre-cancer or cancer. Various cancer types or pre-cancer types may be associated with the presence of the same methylation marker(s) in the urine of an individual presenting with the pre-cancer or cancer. Detection of such markers is indicative for the presence in the individual of one or more of the pre-cancers or cancers that the detected marker(s) are associated with. Such methylation markers are sometimes also referred to as common markers. Common markers are particularly suited to detect whether an individual has cancer or pre-cancer per se.

Detection of one methylation marker in the urine of an individual is indicative for the presence of a cancer or pre-cancer in the individual. Testing for more than one methylation marker in the urine typically allows for the more accurate determination of whether the individual has pre-cancer or cancer. Testing for more than one methylation marker in the urine typically allows for the more accurate typing of the pre-cancer or the cancer that the individual has. Markers that are common to many different types of cancer or pre-cancer are typically used in methods of the invention for determining whether an individual has cancer. Markers that are not shared by many pre-cancers or cancers, and preferably markers that are tumor-specific are typically used to type the pre-cancer or the cancer that the individual.

A method of the invention may simultaneously detect that an individual from which the urine was tested has cancer or pre-cancer and type the cancer or pre-cancer.

As used herein, the term "a polynucleotide primer/probe" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.) or sugar moiety, in addition, the bases in a primer/probe may be joined by a linkage other than a phosphodiester bond, so long as it does not interfere with hybridization. Thus, for example, primer/probes may be peptide nucleic acids in which the constituent bases are joined by peptide bonds rather than phosphodiester linkages. It will be understood by one of skill in the art that probes may bind target sequences lacking complete complementarity with the primer/probe sequence depending upon the stringency of the hybridization conditions. The primers/probes are preferably directly labeled as with isotopes, chromophores, lumiphores, chromogens, or indirectly labeled such as with biotin to which a streptavidin complex may later bind. By assaying for the presence or absence of the primer/probe, one can detect the presence or absence of the select sequence or subsequence.

As used herein, the term "methylation" refers to the covalent attachment of a methyl group at the C5-position of the nucleotide base cytosine within the CpG dinucleotides of gene regulatory region. The term "hypermethylation" refers to the methylation state corresponding to an increased presence of 5-methyl-cytosine ("5-mCyt") at one or a plurality of CpG dinucleotides within a DNA sequence of a test sample, relative to the amount of 5-mCyt found at corresponding CpG dinucleotides within the DNA sequence of a sample of a normal individual or cell of the same type as the test sample. The term "methylation state" or "methylation status" or "methylation level" or "the degree of methylation" refers to the presence or absence of 5-mCyt at one or a plurality of CpG dinucleotides within a DNA sequence. As used herein, the terms "methylation status" or "methylation state" or "methylation level" or "degree of methylation" are used interchangeably.

As used here, the term "CpG islands" are short DNA sequences rich in the CpG dinucleotide and defined as sequences greater than 200 bp in length, with a GC content greater than 0.5 and an observed to expected ratio based on GC content greater than 0.6. See Gardiner-Garden and Frommer, "CpG islands in vertebrate genomes," J Mol Biol 196(2): 261-282 (1987). CpG islands were associated with the 5' ends of all housekeeping genes and many tissue-specific genes, and with the 3' ends of some tissue-specific genes. A few genes contain both the 5' and the 3' CpG islands, separated by several thousand base pairs of CpG-depleted DNA. The 5' CpG islands extended through 5'-flanking DNA, exons, and introns, whereas most of the 3' CpG islands appeared to be associated with exons. CpG islands are generally found in the same position relative to the transcription unit of equivalent genes in different species, with some notable exceptions. CpG islands have been estimated to constitute 1%-2% of the mammalian genome, and are found in the promoters of all housekeeping genes, as well as in a less conserved position in 40% of genes showing tissue-specific expression. The persistence of CpG dinucleotides in CpG islands is largely attributed to a general lack of methylation of CpG islands, regardless of expression status. The term "CpG site" refers to the CpG dinucleotide within the CpG islands. CpG islands are typically, but not always, between about 0.2 to about 1 kb in length.

As used herein, "detecting" refers to the identification of the presence or absence of a target nucleic acid molecule comprising the methylation marker in a urine sample. As used herein, "detecting" also refers to detecting the presence of the target nucleic acid molecule during a process wherein the signal generated by a directly or indirectly labeled probe nucleic acid molecule (capable of hybridizing to the target) is measured or observed. Thus, detection of the probe nucleic acid is directly indicative of the presence, and thus the detection, of a target nucleic acid, such as a sequence encoding a marker gene. For example, if the detectable label is a fluorescent label, the target nucleic acid is "detected" by observing or measuring the light emitted by the fluorescent label on the probe nucleic acid when it is excited by the appropriate wavelength, or if the detectable label is a fluorescence/quencher pair, the target nucleic acid is "detected" by observing or measuring the light emitted upon association or dissociation of the fluorescence/quencher pair present on the probe nucleic acid, wherein detection of the probe nucleic acid indicates detection of the target nucleic acid. If the detectable label is a radioactive label, the target nucleic acid, following hybridization with a radioactively labeled probe is "detected" by, for example, autoradiography. Methods and techniques for "detecting" fluorescent, radioactive, and other chemical labels maybe found in Ausubel et al. (1995, Short Protocols in Molecular Biology, 3r Ed. John Wiley and Sons, Inc.). Alternatively, a nucleic acid may be "indirectly detected" wherein a moiety is attached to a probe nucleic acid which will hybridize with the target, such as an enzyme activity, allowing detection in the presence of an appropriate substrate, or a specific antigen or other marker allowing detection by addition of an antibody or other specific indicator. Alternatively, a target nucleic acid molecule can be detected by amplifying a nucleic acid sample prepared from a patient clinical sample, using oligonucleotide primers which are specifically designed to hybridize with a portion of the target nucleic acid sequence. Quantitative amplification methods, such as, but not limited to TaqMan, may also be used to "detect" a target nucleic acid according to the invention. A nucleic acid molecule is "detected" as used herein where the level of nucleic acid measured (such as by quantitative PCR), or the level of detectable signal provided by the detectable label is at all above the background level.

As used herein, "detecting" further refers to detecting methylation state or status on a specific CpG site of a target nucleic acid molecule that is indicative of a pre-cancer or cancer condition of the individual and or the type of pre-cancer or cancer. The methylation state or status on a specific CpG site of a target nucleic acid molecule can provide useful information for diagnosis, disease monitoring, and therapeutic approaches. Various methods known in the art may be used for determining the methylation status of specific CpG dinucleotides. Such methods include but are not limited to methylated CpG island amplification, see Toyota et al., "Identification of differentially methylated sequences in colorectal cancer by methylated CpG island amplification," Cancer Res., 59: 2307-2312 (1999), see also WO00/26401A1; differential methylation hybridization, see Huang et al., "Methylation profiling of CpG islands in human breast cancer cells," Hum. Mol. Genet, 8: 459-470 (1999); methylation-specific PCR (MSP), see Herman et al, "Methylation-specific PCR: a novel PCR assay for methylation status of CpG islands," PNAS USA 93: 9821-9826 (1992), see also U.S. Pat. No. 5,786,146; methylation-sensitive single nucleotide primer extension (Ms-SnuPE), see U.S. Pat. No. 6,251,594; combined bisulfite restriction analysis (COBRA), see Xiong and Laird, "COBRA: a sensitive and quantitative DNA methylation assay," Nucleic Acids Research, 25(12): 2532-2534 (1997); and methylation-specific primer extension (MSPE), etc A methylation marker is detected (present) when the marker CpG dinucleotide is methylated. A methylation marker is not detected (absent) when the marker CpG dinucleotide comprising the marker is not methylated.

A method of the invention comprises determining the presence or absence of one or more methylation marker of a methylation marker set in urine. A methylation marker is detected (present) when the marker CpG dinucleotide is methylated. A methylation marker is not detected (absent) when the marker CpG dinucleotide comprising the marker is not methylated. In a preferred embodiment the presence or absence of two or more methylation markers of a methylation marker set is determined. In a preferred embodiment the presence or absence of three or more, preferably four or more methylation markers of a methylation marker set are detected. The methylation marker set preferably comprises at least one methylation marker selected from the group consisting of the methylation markers identified in Table 9. The methylation marker set preferably comprises, and more preferably consists of the methylation marker set of Table 9. Determining the presence or absence of more than one methylation marker is helpful in case where the presence of one methylation marker is associated with more than one type of cancer or pre-cancer. In such cases more methylation markers are preferred. In such cases as many methylation markers as needed to discriminate between the cancers are preferably determined.

Detection of the presence of at least one methylation marker in a promoter region of at least one of the genes RASSF1A, ZNF154, TMEFF2, GDF15, CDKN2A, SHOX2, SOX17, GATA2, 3OST2, CYGB, FAM19A4, PHACTR3 and APC of Table 9 indicates that the individual has lung cancer, preferably non-small cell lung cancer. In a preferred embodiment at least one methylation marker in a promoter region of at least two of the genes RASSF1A, ZNF154, TMEFF2, CDKN2A, SHOX2, SOX17, GATA2, 3OST2, CYGB, FAM19A4, PHACTR3 and APC of Table 9 are detected to indicated that the individual has lung cancer, preferably non-small cell lung cancer. In a preferred embodiment methylation markers in a promoter region of at least three and preferably at least four of the genes RASSF1A, ZNF154, TMEFF2, CDKN2A, SHOX2, SOX17, GATA2, 3OST2. CYGB, FAM19A4, PHACTR3 and APC of Table 9 are detected to indicated that the individual has lung cancer, preferably non-small cell lung cancer. In case of determining whether an individual has lung cancer it is preferred that the presence or absence of a methylation marker in a promoter region of the gene RASSF1A is determined. In a preferred embodiment a methylation marker in a promoter region of the gene RASSF1A and at least one of the genes GATA2, 3OST2, GDF15, TMEFF2 is determined. In a preferred embodiment the presence or absence of a methylation marker in a promoter region of the gene RASSF1A and at least one, and preferably at least two, preferably at least three and more preferably four of the genes GATA2, 3OST2, GDF15, TMEFF2 is determined. In another embodiment of determining whether an individual has lung cancer it is preferred that the presence or absence of a methylation marker in a promoter region of the gene CYGB, FAM19A4 or PHACTR3 is determined. In another embodiment of determining whether an individual has lung cancer it is preferred that the presence or absence of a methylation marker in a promoter region of the gene CYGB is determined. In another embodiment of determining whether an individual has lung cancer it is preferred that the presence or absence of a methylation marker in a promoter region of the gene CYGB and at least one of FAM19A4 or PHACTR3 is determined. In a preferred embodiment a methylation marker in a promoter region of the gene CYGB and at least one of the genes GATA2, 3OST2, GDF15, TMEFF2 is determined. In a preferred embodiment the presence or absence of a methylation marker in a promoter region of the gene CYGB and at least one, and preferably at least two, preferably at least three and more preferably four of the genes GATA2, 3OST2, GDF15, TMEFF2, FAM19A4 or PHACTR3 is determined. Extending the panel of methylation markers increases the accuracy of the method.

Detection of the presence of at least one methylation marker in a promoter region of at least one of the genes GDF15, TMEFF2, VIM, TWIST1, NID2, ZNF154 and RASSF1A of Table 9 indicates that the individual has an Urothelial cell carcinoma such as bladder cancer. In a preferred embodiment at least one methylation marker in a promoter region of at least two of the genes GDF15, TMEFF2, VIM, TWIST1, NID2, ZNF154 and RASSF1A of Table 9 are detected to indicated that the individual has an Urothelial cell carcinoma such as bladder cancer. In a preferred embodiment methylation markers in a promoter region of at least three and preferably at least four of the genes GDF15; TMEFF2, VIM, TWIST1, NID2, ZNF154 and RASSF1A of Table 9 are detected to indicated that the individual has an Urothelial cell carcinoma such as bladder cancer. In case of determining whether an individual has an Urothelial cell carcinoma such as bladder cancer it is preferred that the presence or absence of a methylation marker in a promoter region of the gene GDF15 is determined. In a preferred embodiment a methylation marker in a promoter region of the gene GDF15 and at least one and preferably at least two, and more preferably three of the genes TMEFF2, VIM, and RASSF1A is determined.

Detection of the presence of at least one methylation marker in a promoter region of at least one of the genes CYGB, SFRP2A and MGMT of Table 9 indicates that the individual has an colon cancer. In a preferred embodiment at least one methylation marker in a promoter region of at least two of the genes CYGB, SFRP2A and MGMT of Table 9 are detected to indicate that the individual has colon cancer. In a preferred embodiment methylation markers in a promoter region of at least three of the genes CYGB, SFRP2A and MGMT of Table 9 are detected to indicated that the individual has colon cancer. In case of determining whether an individual has colon cancer it is preferred that the presence or absence of a methylation marker in a promoter region of the gene CYGB is determined. In a preferred embodiment methylation markers in a promoter region of at least two of the genes CYGB and MGMT of Table 9 are determined to indicated that the individual has colon cancer.

Extending the panel of methylation markers increases the accuracy of the method.

Detection of the presence of at least one methylation marker in a promoter region of at least one of the genes FAM19A4, PHACTR3, PRDM14, CAD M1, MAL and miR124-2 of Table 9 indicates that the individual has cervical cancer. In a preferred embodiment at least one methylation marker in a promoter region of at least two of the genes FAM19A4, PHACTR3, PRDM14, CAD M1, MAL and miR124-2 of Table 9 are detected to indicated that the individual has cervical cancer. In a preferred embodiment methylation markers in a promoter region of at least three and preferably at least four, preferably at least 5 of the genes, more preferably at least six of the genes FAM19A4, PHACTR3, PRDM14, CAD M1, MAL and miR124-2 of Table 9 are detected to indicated that the individual has cervical cancer. In case of determining whether an individual has cervical cancer it is preferred that the presence or absence of a methylation marker in a promoter region of the gene FAM19A4, the gene PRDM14 or preferably a combination thereof, is determined. It is preferred that the presence or absence of a methylation marker in a promoter region of the gene FAM19A4, the gene PRDM14 or preferably a combination thereof, is determined together with the presence or absence of a methylation marker in a promoter of one, two, three or preferably four of the genes MAL, miR124-2, PHACTR3 and CADM1. Extending the panel of methylation markers increases the accuracy of the method.

Detection of the presence of at least one methylation marker in a promoter region of the gene GSTP1 of Table 9 indicates that the individual has prostate cancer.

Some markers are detected in more than one tumor. In such cases the marker is particularly suited to indicate that an individual has cancer or pre-cancer. The type of (pre-) cancer can be determined by other diagnostic means and/or by including more methylation makers in the test.

A method of the invention may indicate that an individual has (pre-)cancer. In such a case the invention can often also indicate what the tissue of origin (the primary tumor site) of the cancer is. Indicating that an individual has a colon cancer does not mean that the cancer has to be located in the colon. The tumor can have metastasized and be present at a different location.

A method of the invention may indicate that an individual has cancer. More often though the method indicates that the tested individual has a significant chance of having cancer or pre-cancer. It is recommended that the individual has further tests to make the diagnosis cancer. In one aspect, a method of the invention is a selection method for individuals that have a higher than normal chance of having a pre-cancer or cancer.

Detection of the presence or absence of pre-cancer or cancer in an individual is preferably determined by determining the presence or absence of a methylation marker in a promoter region of a gene FAM19A4; RASSF1A or ZNF154 of table 9. In a preferred embodiment the detection of the presence or absence of pre-cancer or cancer in an individual is determined by determining the presence or absence of a methylation marker in a promoter region of a gene FAM19A4; RASSF1A of table 9 and a methylation marker in a promoter region of ZNF154 of table 9, and preferably the combination thereof. Determining that the methylations markers in a promoter region of a gene FAM19A4; or RASSF1A of table 9 and/or ZNF154 of table 9 are absent indicates that the individual from which the urine was collected, does not have, or does no longer have pre-cancer or cancer.

Detection of the presence or absence of methylation markers as disclosed in the present invention preferably comprises amplification of nucleic acid in the urine sample. Preferably detection of the presence of at least one methylation marker comprises amplification of nucleic acid of at least 15, preferably at least 30, preferably at least 50, preferably at least 100 and more preferably 150 consecutive nucleotides of a nucleic acid in the urine sample of the individual. Preferably at least one methylation marker is a CpG island in a promoter region of a gene identified in Table 9.

A methylation marker preferably comprises methylation of one or more CpG's in a CpG island in a promoter region of a gene listed in Table 9. A methylation marker of table 9 is thus methylation of one or more CpG's in a CpG island of a promoter region of a gene listed in table 9. One way of designing primers for methylation specific PCR (preferably quantitative PCR) to detect this methylation is discussed in Davidovic et al. and Snellenberg et al. [1, 2].

Determining a pre-cancer or cancer type preferably comprises detecting the presence of at least one methylation marker of Table 9 in the urine sample of the individual. The presence of a methylation marker of Table 9 indicates that the individual has cancer or pre-cancer. Subsequently the presence of a particular methylation marker typically includes certain pre-cancers or cancers in the typing. The absence of a certain other methylation marker can exclude a certain type from the list of types of pre-cancer or cancer. So both the presence and the absence can be indicative for certain types of pre-cancer or cancer. Determining that an individual does not have a cancer or a pre-cancer preferably comprises determining the absence of methylation markers in a promoter of two or more of the genes described in table 9. Preferably in a promoter of at least three, four, five, six, seven or more of the genes described in table 9.

The invention further provides a method for population screening of individuals for the occurrence of cancer or pre-cancer comprising collecting urine samples for said population of individuals and determining the presence or absence of one or more methylation markers of a methylation marker set said urine samples; and determining whether there are individuals with cancer or pre-cancer based on the detection of the presence or absence of said one or more methylation markers in the urine samples, wherein the presence of said one or more methylation markers indicates that an individual of the population has pre-cancer or cancer and the absence of the methylation markers indicates that of the population does not have pre-cancer or cancer. The one or more methylation markers are preferably methylation markers of the invention, such as the methylation markers described in table 9.

Population screening, or testing a urine sample for determining whether an individual has cancer or pre-cancer is preferably performed on a urine sample or urine samples (in case of screening) of individual(s) of which it is not known what the cancer or pre-cancer status is.

The sample of the present invention is a urine sample. In a preferred embodiment the sample is a cell free urine sample. Cell free samples may be collected by filtration of urine or by centrifugation and collection of the supernatant. Other methods to essentially remove intact cells from a collected urine sample are known in the art and are also useful in the present invention. Typically, albeit not necessarily always, larger cell debris is also removed from the urine prior to performing a method of the invention. A cell as defined in the present invention is a cell that contains a nucleus. Erythrocytes can be present in urine and are preferably also removed. Cell free samples are suitably collected by harvesting supernatant after centrifugation at 3000×g.

The invention further provides a nucleic acid amplification device wherein preferably the methylation marker set comprises at least one means for detecting a methylation marker selected from the group consisting of the methylation markers identified in Table 9. In a preferred embodiment the device comprises nucleic acid amplification primers for amplifying nucleic acid comprising the methylation markers from the methylation marker set of Table 1.

EXAMPLES

Materials & Methods

All urine samples were supplied by volunteers under full consent. Since the urine is a 'waste product' that is acquired non-invasively, no approval the medical and ethical overview board was required. Nevertheless, all subjects were asked permission for the use of their urine.

We collected urine of 20 patients with bladder cancer like symptoms, 20 patients with confirmed cervical cancer. In a first experiment we tested urine samples of 20 lung cancer patients and 10 healthy individuals. In a second experiment we tested 14 independent urine samples of lung cancer patients and 19 controls. We also tested urine samples of 11 patients with colon cancer and 22 control. For the cervical cancer patients routine methylation tests based on cervical swabs were compared to our results.

We investigate the promoter region methylation of the genes RASSF1A, VIM, GDF15 and TMEFF2 for bladder cancer, APC, GATA2, 3OST2, RASSF1A, GDF15, TMEFF2 VIM, GYGB, FAM19A4, and PHACTR3 for lung cancer, FAM19A4, PHACTR3, PRDM14, CAD M1, MAL and miR124-2 for cervical cancer, and CYGB, SFRP2A and MGMT for colon cancer.

TABLE 1 used primer sequences per gene in qPCR.

| Gene | Forward | Reverse |
|---|---|---|
| GDF15 | TCG GCG GTT ATT TGT ATT TGC | CGT CGA AAA CAA CCG AAA CA |
| TMEFF2 | GTT CGG GGT TAC GCG C | TTC GCC TCA CTC TCC GCT |
| VIM | TTC GGG AGT TAG TTC GCG TT | ACC GCC GAA CAT CCT ACG A |
| RASSF1A | GCG TTG AAG TCG GGG TTC | CCC GTA CTT CGC TAA CTT TAA ACG |
| GATA2 | GCG GTC GTT CGG CGT GTC | AAA CGA ACC GAA CCG AAA ACG |
| APC | GAA CCA AAA CGC TCC CCA T | TTA TAT GTC GGT TAC GTG CGT TTA TAT |
| 3OST2 | TCG GCG TAC GTA AGA GTT TGG | ATC TCC CGA TCC TAA ACG ATA AAA |
| FAM19A4 | AGT CGG GCG GTT CGG TT | CAA AAC GAC GCG CAA CT |
| PHACTR3 | GGT TAT TTT GCG AGC GGT TTC | CGA ATA CTC TAA TTC CAC GCG ACT |
| PRDM14 | TTA CGT GTT ATT GTC GGG GAT T | ATC TAT TCC TAA TAC CTA AAA ACG AAA CG |
| CADM1 | CGT ATG TTA TTA GTA TTT TAT TAG TTG TTC GTT C | CGC TCG ACA ACA CTA CAC TCG |
| MAL | GGT TAT TGG GTT TCG CG | GTA CTA ACG TCG ACC TTA AAA CGA |
| mir124-2 | GGT AAT TAA TTT GGA TTT ACG TCG TTA T | CGT AAA AAT ATA AAC GAT ACG TAT ACC TAC GT |
| β-actin | TGG TGA TGG AGG AGG TTT AGT AAG T | AAC CAA TAA AAC CTA CTC CTC CCT TAA |
| CYGB | CGA GGT CGA TCG TTA GTT CGT TC | CCA ACG ACT AAC TCG AAA ACG CG |
| SFRP2 | CGT TTT AGT CGT CGG TTG TTA GTT T | TCC CGA ACC CGC TCT CTT |
| MGMT | GAT TTT TAT TAA GCG GGC GTC | CTT TTC CTA TCA CAA AAA TAA TCC G |

Figure 2:
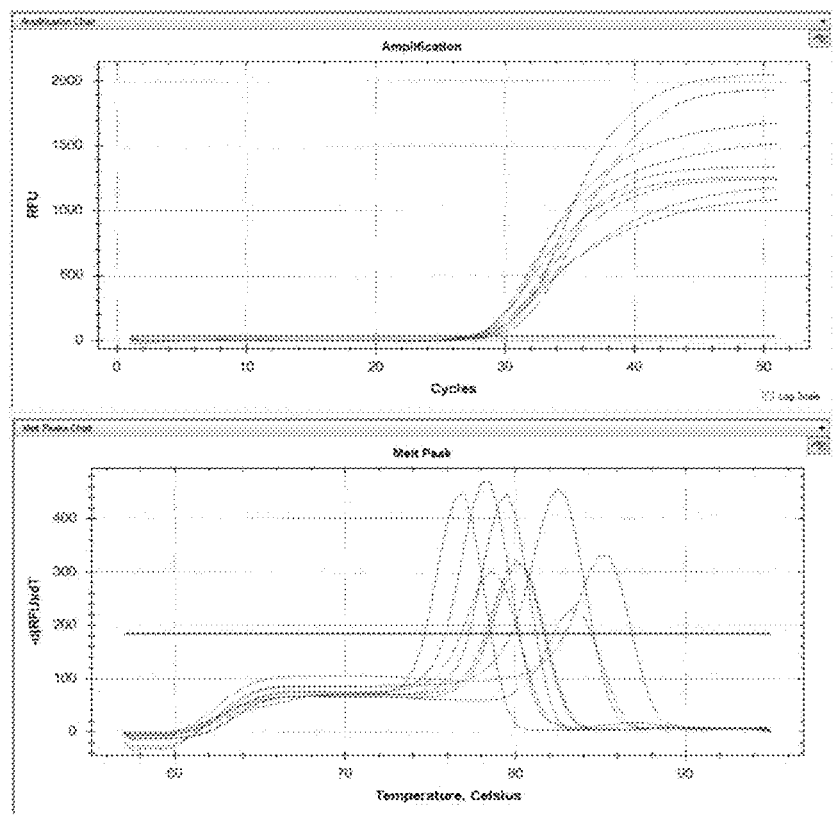
FIG. 2: an example of a methylation specific qPCR results. Shown are both the amplification plots (top graph) of multiple genes and the product melting curves. Clearly seen is the different melting temperature for different amplicons (lower graph).

DNA was extracted from the urine samples (5-40 mL urine per extraction, dependent on availability) with the Zymo research 'Quick-DNA™ Urine' kit according to protocol. The DNA was subsequently treated with bisulfite (Zymo research 'EZ DNA Methylation™' Kit according to protocol). The resulting bisulfite treated DNA was used for methylation specific qPCR (MSP) in a BIORAD real time CFX 384, using iQ SYBR Green supermix or on an ABI-7500 real-time PCR-system (Applied Biosystems). The results were analyzed using machine specific software (see FIG. 2 for a data example).

Results

With respect to blood, urine already contains a concentrate of the 'waste products' of the body, due to initial filtration and consecutive active resorption of useful compounds. Furthermore, urine is available in greater quantities than blood, allowing us to start with up to 40 mL urine. By eluting the DNA from that urine in 10 μL $H_2O$ a concentration step of 4000× is achieved on top of the concentration done by the kidneys prior to quantitative PCR (qPCR).

All qPCR samples were simultaneously tested for the presence of the gene ß-actin, which is used here as a methylation independent marker. This was used to assess whether enough DNA for qPCR was present in the urine sample. Some samples do not contain (sufficient) DNA.

The qPCR results of the bladder cancer samples showed 12 out of 20 with enough DNA in the sample and out of these 12, 11 were positive for one or more of our methylation markers.

TABLE 2 genes detected in the urine of bladder cancer patients with sufficient DNA concentrations for MSP analysis. These urine samples were tested for GDF15, TMEFF2, VIM and RASSF1A.

| Sample # | Detected gene methylation | | |
|---|---|---|---|
| 2 | GDF15 | TMEFF2 | RASSF1A |
| 3 | GDF15 | TMEFF2 | VIM |
| 7 | GDF15 | TMEFF2 | RASSF1A |
| 8 | GDF15 | TMEFF2 | |
| 11 | GDF15 | TMEFF2 | |
| 12 | — | | |
| 14 | GDF15 | TMEFF2 | |
| 15 | GDF15 | TMEFF2 | |
| 17 | GDF15 | TMEFF2 | VIM |
| 18 | GDF15 | TMEFF2 | VIM |
| 19 | GDF15 | TMEFF2 | VIM |
| 20 | GDF15 | TMEFF2 | |

The urines of cervical cancer patients were used to compare the methylation patterns of swabs with spontaneous urines and catheter urines. Similar methylation patterns were be seen in the urine and swab samples. The catheter urine (which has no contact with tumor cells or tumor cell debris) showed clear methylation of our marker genes as seen in table 3 below. The 5 healthy female control subjects were all negative for all 6 markers in urine.

TABLE 3 genes detected in the urine of cervical cancer patients compared to cervical swabs. Not all samples were available for each patient. The reference to FAM is a reference to the gene FAM19A4.

| Patient | sample type | DNA Control | FAM | PHACTR3 | PRDM14 | CADM1 | MAL | miR124-2 |
|---|---|---|---|---|---|---|---|---|
| #1 | Swab | ok | FAM | PHACTR3 | PRDM14 | n.a. | n.a. | n.a. |
| | urine (catheter) | ok | — | — | — | — | — | — |
| #2 | Swab | not sufficient | — | — | — | n.a. | n.a. | n.a. |
| | urine (catheter) | ok | FAM | — | PRDM14 | — | — | — |

TABLE 3-continued genes detected in the urine of cervical cancer patients compared to cervical swabs. Not all samples were available for each patient. The reference to FAM is a reference to the gene FAM19A4.

| Patient | sample type | DNA Control | FAM | PHACTR3 | PRDM14 | CADM1 | MAL | miR124-2 |
|---|---|---|---|---|---|---|---|---|
| #3 | Swab | not sufficient | — | — | — | n.a. | n.a. | n.a. |
|  | urine (catheter) | ok | — | — | PRDM14 | — | MAL | — |
| #4 | Swab | ok | FAM | PHACTR3 | PRDM14 | n.a. | n.a. | n.a. |
|  | urine (catheter) | ok | FAM | PHACTR3 | PRDM14 | CADM1 | MAL | miR124-2 |
| #5 | Swab | ok | — | — | — | n.a. | n.a. | n.a. |
|  | urine (catheter) | ok | — | — | PRDM14 | — | — | — |
| #6 | Swab | not sufficient | — | — | — | n.a. | n.a. | n.a. |
|  | urine (catheter) | not sufficient | — | — | — | n.a. | n.a. | n.a. |
| #7 | Swab | not sufficient | — | — | — | n.a. | n.a. | n.a. |
|  | urine (catheter) | ok | FAM | — | PRDM14 | CADM1 | MAL | miR124-2 |
| #8 | Swab | ok | FAM | — | — | n.a. | n.a. | n.a. |
|  | urine (catheter) | ok | FAM | — | PRDM14 | — | MAL | — |
| #9 | Swab | not sufficient | — | — | — | n.a. | n.a. | n.a. |
|  | urine (catheter) | ok | — | — | — | — | MAL | miR124-2 |
| #10 | Swab | not sufficient | — | — | — | n.a. | n.a. | n.a. |
|  | urine (catheter) | ok | FAM | — | PRDM14 | — | — | — |
|  | Urine (spontaneous) | ok | FAM | — | PRDM14 | — | — | — |
| #11 | Swab | not sufficient | — | — | — | n.a. | n.a. | n.a. |
|  | Urine (spontaneous) | not sufficient | — | — | — | n.a. | n.a. | n.a. |
| #12 | Swab | not sufficient | — | — | — | n.a. | n.a. | n.a. |
|  | urine (catheter) | ok | FAM | PHACTR3 | PRDM14 | — | MAL | miR124-2 |
|  | Urine (spontaneous) | ok | FAM | PHACTR3 | PRDM14 | — | MAL | miR124-2 |
| #13 | Swab | not sufficient | — | — | — | n.a. | n.a. | n.a. |
|  | urine (catheter) | ok | FAM | — | PRDM14 | — | MAL | miR124-2 |
|  | Urine (spontaneous) | ok | FAM | — | PRDM14 | — | MAL | miR124-2 |
| #14 | Swab | not sufficient | — | — | — | n.a. | n.a. | n.a. |
|  | urine (catheter) | ok | FAM | PHACTR3 | PRDM14 | CADM1 | MAL | miR124-2 |
| #15 | Swab | not sufficient | — | — | — | n.a. | n.a. | n.a. |
|  | urine (catheter) | ok | FAM | PHACTR3 | PRDM14 | — | — | — |
|  | Urine (spontaneous) | ok | FAM | PHACTR3 | PRDM14 | — | MAL | miR124-2 |
| #16 | Swab | not sufficient | — | — | — | n.a. | n.a. | n.a. |
|  | Urine (spontaneous) | ok | — | PHACTR3 | — | — | — | — |
| #17 | Swab | not sufficient | — | — | — | n.a. | n.a. | n.a. |
|  | urine (catheter) | ok | — | — | PRDM14 | — | — | — |
|  | Urine (spontaneous) | ok | FAM | PHACTR3 | PRDM14 | CADM1 | MAL | miR124-2 |
| #18 | Swab | not sufficient | — | — | — | n.a. | n.a. | n.a. |
|  | urine (catheter) | ok | FAM | — | PRDM14 | — | MAL | — |
|  | Urine (spontaneous) | ok | FAM | PHACTR3 | — | CADM1 | MAL | miR124-2 |
| #19 | Swab | not sufficient | — | — | — | n.a. | n.a. | n.a. |
|  | urine (catheter) | ok | FAM | — | PRDM14 | — | — | — |
| #20 | Swab | not sufficient | — | — | — | n.a. | n.a. | n.a. |
|  | urine (catheter) | ok | — | PHACTR3 | — | — | — | miR124-2 |
|  | Urine (spontaneous) | ok | FAM | PHACTR3 | PRDM14 | — | — | — |

The presence of methylated DNA sequences in the catheter urine of the cervical cancer patients indicates the ability of the methylation markers to reach the urine without direct contact of the urine with the tumor, because catheter urine does not pass the vulva which excludes cervical, vaginal and vulvar contamination. To confirm that tumor-derived methylated DNA sequences reach the urine without direct contact, a non-genitourinary cancer was investigated excluding the possibility of ex vivo contamination: lung cancer. 2 sets of patient samples were analyzed with 2 different methylation marker panels.

Only patients with a positive signal on the β-actin control gene are listed in table 4. In the first sample set, we found enough DNA (β-actin methylation independent control) in 19 out of 27 samples. Samples were tested for RASSF1A, GATA2, 3OST2, APC, GDF15, TMEFF2, and VIM. Of these 19 samples 11 showed hypermethylation of the promoter regions of the genes named below.

TABLE 4 methylated markers found in urine from lung cancer patients.

| patient | positive genes | | | | |
|---|---|---|---|---|---|
| 1 | — | | | | |
| 2 | RASSF1A | APC | GATA2 | 3OST2 | TMEFF2 |
| 3 | RASSF1A | GATA2 | GDF15 | | |
| 4 | RASSF1A | | | | |
| 5 | RASSF1A | | | | |
| 6 | RASSF1A | TMEFF2 | | | |
| 10 | — | | | | |
| 11 | — | | | | |
| 12 | GDF15 | | | | |
| 14 | RASSF1A | | | | |
| 15 | — | | | | |
| 16 | — | | | | |
| 18 | RASSF1A | | | | |
| 20 | RASSF1A | | | | |
| 21 | 3OST2 | | | | |
| 22 | — | | | | |
| 23 | — | | | | |
| 24 | 3OST2 | VIM | GDF15 | | |
| 26 | — | | | | |

Out of the 10 healthy controls in this sample set, 8 had a positive β-actin signal. Of these 8 samples 2 showed methylation positivity for one or two markers (table 5), indicating the necessity of cut-off values for this test.

TABLE 5 control samples tested in combination with the lung cancer samples.

| Control | | |
|---|---|---|
| 2 | — | |
| 3 | — | |
| 4 | — | |
| 5 | — | |
| 6 | RASSF1A | GDF15 |
| 7 | — | |
| 9 | RASSF1A | |
| 10 | — | |

In the second sample set, 14 patient samples had a positive b-actin signal. Of these 14 samples, 11 showed hypermethylation of the promoter regions of 3 genes named CYGB, FAM19A4 and PHACTR3 above a certain threshold value (table 6). In zero out of 19 healthy control samples with a positive b-actin signal, these 3 markers were detected above the same threshold. A fourth methylation marker investigated: PRDM14 was identified in 12 of the 14 patient samples, but was also identified in 8 out of the 19 control samples (Table 7). This indicates that not all hypermethylated DNA sequences previously identified in tumors have a strong diagnostic power in urine samples.

TABLE 6 methylated markers found in urine from lung cancer patients.

| patient | postive genes | | |
|---|---|---|---|
| 1 | | FAM19A4 | PRDM14 |
| 3 | | FAM19A4 | PHACTR3 | PRDM14 |
| 4 | — | | | PRDM14 |
| 5 | CYGB | FAM19A4 | | PRDM14 |
| 6 | CYGB | FAM19A4 | | PRDM14 |
| 8 | — | | | |
| 9 | | FAM19A4 | | |
| 10 | | | PHACTR3 | PRDM14 |
| 11 | — | | | PRDM14 |
| 13 | CYGB | | | PRDM14 |
| 15 | | | PHACTR3 | PRDM14 |
| 16 | CYGB | | | PRDM14 |
| 17 | | FAM19A4 | | PRDM14 |
| 18 | | FAM19A4 | | PRDM14 |

TABLE 7 methylated markers found in urine from healthy controls.

| control | | |
|---|---|---|
| 1 | — | PRDM14 |
| 2 | — | PRDM14 |
| 3 | — | |
| 4 | — | |
| 5 | — | |
| 6 | — | PRDM14 |
| 8 | — | PRDM14 |
| 9 | — | PRDM14 |
| 10 | — | |
| 11 | — | |
| 12 | — | PRDM14 |
| 13 | — | |
| 14 | — | |
| 16 | — | |
| 17 | — | |
| 19 | — | |
| 20 | — | |
| 21 | — | PRDM14 |
| 22 | — | PRDM14 |

Figure 1:
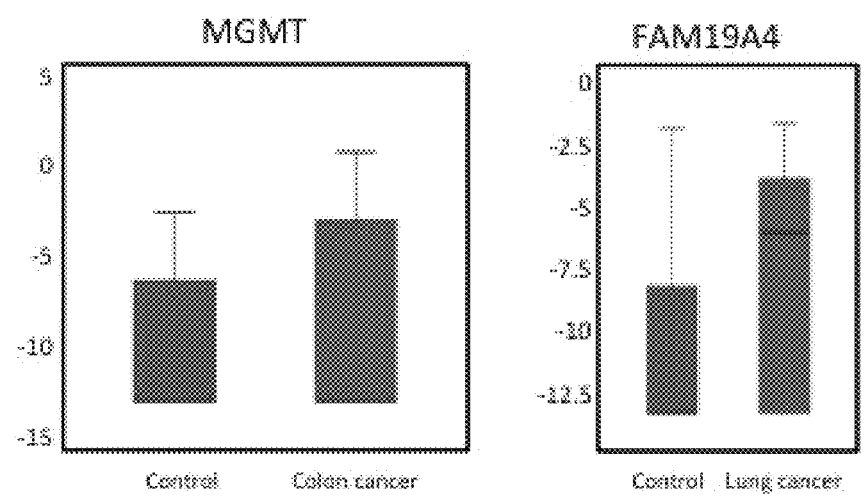
FIG. 1: example of qPCR results of 2 methylation markers in urine of cancer patients (red) and urine of healthy controls (green). Boxplots are shown presenting the methylation level of respectively MGMT and FAM19A4 relative to the housekeeping gene B-actin on a logarithmic scale. MGMT is an example of a marker for which no discriminatory power between cancer patients and healthy controls was detected. FAM19A4 is an example of a marker with good discriminatory power.

To further establish the conclusion that at least some hypermethylated DNA sequences from tumors that are not in contact with urine do reach the urine and can be detected in urine samples of patients, we tested another set of urine samples from patients with a non-genitourinary cancer: colon cancer. 11 urine samples had a positive b-actin signal. These samples were tested for 3 methylation markers: CYGB, SFRP2 and MGMT. All of these markers were detectable in the urine of cancer patients. Of these 3 markers only CYGB was more often detected in the urine of patients compared to healthy controls (see table 7). The absence of discriminatory power for MGMT is shown in FIG. 1. This again underscores that not all methylated DNA sequences identified in tumors can be used as cancer-selective markers in urine samples.

TABLE 8 methylated markers found in urine from colon cancer patients and healthy controls.

| patient | postive genes | | control | |
|---|---|---|---|---|
| 1 | | SFRP2 | 1 | SFRP2 |
| 2 | CYGB | SFRP2 | 2 | SFRP2 |
| 5 | | | 3 | SFRP2 |
| 6 | CYGB | | 4 | SFRP2 |
| 7 | | | 5 | SFRP2 |
| 8 | | | 6 | SFRP2 |
| 9 | | SFRP2 | 8 | SFRP2 |
| 11 | | SFRP2 | 9 | SFRP2 |
| 13 | | SFRP2 | 10 | — |
| 17 | | | 11 | — |
| 20 | CYGB | | 12 | SFRP2 |
| | | | 13 | — |
| | | | 14 | SFRP2 |
| | | | 16 | — |
| | | | 17 | — |
| | | | 19 | — |
| | | | 20 | SFRP2 |
| | | | 21 | SFRP2 |
| | | | 22 | SFRP2 |

FIG. 1 shows an example of qPCR results of 2 methylation markers in urine of cancer patients (red) and urine of healthy controls (green). Boxplots are shown presenting the methylation level of respectively MGMT and FAM19A4 relative to the housekeeping gene B-actin on a logarithmic scale. MGMT is an example of a marker for which no discriminatory power between cancer patients and healthy controls was detected. FAM19A4 is an example of a marker with good discriminatory power.

CONCLUSION

The results show that urine contains sufficient tumor DNA that retains sufficient of its methylation status for detection, even if the urine has no direct contact with the tumor(cells). Furthermore the detected methylated DNA fragments can be linked to the gene specific sequences that are indicative for tumor detection and prediction. Therefore we conclude that the detection of cell free methylated DNA fragments in urine is a viable method for cancer detection and typing.

TABLE 9

Methylation markers of the present invention are present in the CpG islands of the promoter region(s) of the genes indicated in this table. Primers for methylation specific PCR (MSP) can be designed according to guidelines in Davidovic et al and Snellenberg et al [1, 2].

| Gene name | Gene ID # | Location | gene description |
| --- | --- | --- | --- |
| APC | 324 | Chromosome 5, NC_000005.10 (112707505 ... 112846239) | adenomatous polyposis coli |
| GATA2 | 2624 | Chromosome 3, NC_000003.12 (128479422 ... 128493187, complement) | GATA binding protein 2 |
| 3OST2 | 9956 | Chromosome 16, NC_000016.10 (22814203 ... 22916338) | heparan sulfate-glucosamine 3-sulfotransferase 2 |
| RASSF1A | 11186 | Chromosome 3, NC_000003.12 (50329786 ... 50340936, complement) | Ras association domain family member 1 |
| GDF15 | 9518 | Chromosome 19, NC_000019.10 (18386158 ... 18389176) | growth differentiation factor 15 |
| TMEFF2 | 23671 | Chromosome 2, NC_000002.12 (191949046 ... 192194940, complement) | transmembrane protein with EGF like and two follistatin like domains 2 |
| VIM | 7431 | Chromosome 10, NC_000010.11 (17227935 ... 17237593) | vimentin |
| GSTP1 | 2950 | Chromosome 11, NC_000011.10 (67583595 ... 67586653) | glutathione S-transferase pi 1 |
| FAM19A4 | 151647 | Chromosome 3, NC_000003.12 (68731764 ... 68932610, complement) | family with sequence similarity 19 (chemokine (C-C motif)-like), member A4 |
| PHACTR3 | 116154 | Chromosome 20, NC_000020.11 (59577509 ... 59847711) | phosphatase and actin regulator 3 |
| PRDM14 | 63978 | Chromosome 8, NC_000008.11 (70051126 ... 70071327, complement) | PR domain 14 |
| CADM1 | 23705 | Chromosome 11 NC_000011.10 (115173625 ... 115504523) | cell adhesion molecule 1 |
| MAL | 4118 | Chromosome 2, NC_000002.12 (95025655 ... 95053992) | mal T-cell differentiation protein |
| MIR124-2 | 406908 | Chromosome 8, NC_000008.11 (64379149 ... 64379257) | microRNA 124-2 |
| SHOX2 | 6474 | Chromosome 3, NC_000003.12 (158096011 ... 158106202, complement) | short stature homeobox 2 |
| CDKN2A | 1029 | Chromosome 9, NC_000009.12 (21967752 ... 21995043, complement) | cyclin-dependent kinase inhibitor 2A |
| SOX17 | 64321 | Chromosome 8, NC_000008.11 (54457935 ... 54460896) | SRY-box 17 |
| TWIST1 | 7291 | Chromosome 7, NC_000007.14 (19113047 ... 19117672, complement) | twist family bHLH transcription factor 1 |
| NID2 | 22795 | Chromosome 14, NC_000014.9 (52004802 ... 52069231, complement) | nidogen 2 |
| ZNF154 | 7710 | Chromosome 19, NC_000019.10 (57696275 ... 57709211, complement) | zinc finger protein 154 |
| CYGB | 114757 | Chromosome 17, NC_000017.11 (76527348 ... 76557692, complement) | cytoglobin |
| SFRP2 | 6423 | Chromosome 4, NC_000004.12 (153780590 ... 153789076, complement) | secreted frizzled related protein 2 |
| MGMT | 4255 | Chromosome 10, NC_000010.11 (129467184 ... 129770983) | O-6-methylguanine-DNA methyltransferase |

CITED ART

1. Snellenberg, S., et al., Development of a multiplex methylation-specific PCR as candidate triage test for women with an HPV-positive cervical scrape. BMC Cancer, 2012. 12: p. 551.
2. Davidovic, R. S., et al., Methylation-specific PCR: four steps in primer design. Central European Journal of Biology, 2014. 9(12): p. 1127-1139.

The invention claimed is:

1. A method of determining the presence or absence of methylation markers, the method comprising:
   determining, in a urine sample from an individual, the presence or absence of methylation markers in a CpG island of the promoter region of the genes GATA2, CYGB, FAM19A4, and TMEFF2; and
   wherein the individual has lung cancer.

2. The method according to claim 1, wherein detection of the presence or absence of methylation markers comprises amplification of nucleic acid in the urine sample.

3. The method according to claim 1, wherein the lung cancer is non-small cell lung cancer.

4. The method according to claim 1, wherein determining the presence or absence of methylation markers comprises detecting the absence of at least one methylation marker in the urine sample of the individual.

5. The method according to claim 1, wherein the urine sample is a cell-free urine sample.

6. The method according to claim 1, further comprising determining the presence or absence of a methylation marker in a CpG island of the promoter region of RASSF1A.

* * * * *

SEQUENCE LISTING

<160> NUMBER OF SEQ ID NOS: 34

<210> SEQ ID NO 1
<211> LENGTH: 21
<212> TYPE: DNA

```
<213> ORGANISM: Artificial Sequence
<220> FEATURE:
<223> OTHER INFORMATION: primer

<400> SEQUENCE: 1
tcggcggtta tttgtatttg c                                              21

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
cgtcgaaaac aaccgaaaca                                                20

<210> SEQ ID NO 3
<211> LENGTH: 16
<212> TYPE: DNA
<213> ORGANISM: Artificial Sequence
<220> FEATURE:
<223> OTHER INFORMATION: primer

<400> SEQUENCE: 3
gttcggggtt acgcgc                                                    16

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
ttcgcctcac tctccgct                                                  18

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ttcgggagtt agttcgcgtt                                                20

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
accgccgaac atcctacga                                                 19

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
gcgttgaagt cggggttc                                                  18
```

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
cccgtacttc gctaacttta aacg                                        24

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
gcggtcgttc ggcgtgtc                                               18

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
aaacgaaccg aaccgaaaac g                                           21

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
gaaccaaaac gctccccat                                              19

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
ttatatgtcg gttacgtgcg tttatat                                     27

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
tcggcgtacg taagagtttg g                                           21

<210> SEQ ID NO 14
<211> LENGTH: 24
<212> TYPE: DNA
<213> ORGANISM: Artificial Sequence
<220> FEATURE:

```
<223> OTHER INFORMATION: primer

<400> SEQUENCE: 14
atctcccgat cctaaacgat aaaa                                              24

<210> SEQ ID NO 15
<211> LENGTH: 17
<212> TYPE: DNA
<213> ORGANISM: Artificial Sequence
<220> FEATURE:
<223> OTHER INFORMATION: primer

<400> SEQUENCE: 15
agtcgggcgg ttcggtt                                                      17

<210> SEQ ID NO 16
<211> LENGTH: 17
<212> TYPE: DNA
<213> ORGANISM: Artificial Sequence
<220> FEATURE:
<223> OTHER INFORMATION: primer

<400> SEQUENCE: 16
caaaacgacg cgcaact                                                      17

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
ggttattttg cgagcggttt c                                                 21

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
cgaatactct aattccacgc gact                                              24

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
ttacgtgtta ttgtcgggga tt                                                22

<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20
atctattcct aatacctaaa aacgaaacg                                         29
```

<210> SEQ ID NO 21
<211> LENGTH: 34
<212> TYPE: DNA
<213> ORGANISM: Artificial Sequence
<220> FEATURE:
<223> OTHER INFORMATION: primer

<400> SEQUENCE: 21
cgtatgttat tagtattta ttagttgttc gttc                        34

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
cgctcgacaa cactacactc g                                     21

<210> SEQ ID NO 23
<211> LENGTH: 17
<212> TYPE: DNA
<213> ORGANISM: Artificial Sequence
<220> FEATURE:
<223> OTHER INFORMATION: primer

<400> SEQUENCE: 23
ggttattggg tttcgcg                                          17

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
gtactaacgt cgaccttaaa acga                                  24

<210> SEQ ID NO 25
<211> LENGTH: 28
<212> TYPE: DNA
<213> ORGANISM: Artificial Sequence
<220> FEATURE:
<223> OTHER INFORMATION: primer

<400> SEQUENCE: 25
ggtaattaat ttggatttac gtcgttat                              28

<210> SEQ ID NO 26
<211> LENGTH: 32
<212> TYPE: DNA
<213> ORGANISM: Artificial Sequence
<220> FEATURE:
<223> OTHER INFORMATION: primer

<400> SEQUENCE: 26
cgtaaaaata taaacgatac gtatacctac gt                         32

<210> SEQ ID NO 27
<211> LENGTH: 25
<212> TYPE: DNA
<213> ORGANISM: Artificial Sequence
<220> FEATURE:
<223> OTHER INFORMATION: primer -continued

```
<400> SEQUENCE: 27
tggtgatgga ggaggtttag taagt                                        25

<210> SEQ ID NO 28
<211> LENGTH: 27
<212> TYPE: DNA
<213> ORGANISM: Artificial Sequence
<220> FEATURE:
<223> OTHER INFORMATION: primer

<400> SEQUENCE: 28
aaccaataaa acctactcct cccttaa                                      27

<210> SEQ ID NO 29
<211> LENGTH: 23
<212> TYPE: DNA
<213> ORGANISM: Artificial Sequence
<220> FEATURE:
<223> OTHER INFORMATION: primer

<400> SEQUENCE: 29
cgaggtcgat cgttagttcg ttc                                          23

<210> SEQ ID NO 30
<211> LENGTH: 23
<212> TYPE: DNA
<213> ORGANISM: Artificial Sequence
<220> FEATURE:
<223> OTHER INFORMATION: primer

<400> SEQUENCE: 30
ccaacgacta actcgaaaac gcg                                          23

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
cgttttagtc gtcggttgtt agttt                                        25

<210> SEQ ID NO 32
<211> LENGTH: 18
<212> TYPE: DNA
<213> ORGANISM: Artificial Sequence
<220> FEATURE:
<223> OTHER INFORMATION: primer

<400> SEQUENCE: 32
tcccgaaccc gctctctt                                                18

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
gatttttatt aagcgggcgt c                                            21

<210> SEQ ID NO 34
<211> LENGTH: 25
```

```
<212> TYPE: DNA
<213> ORGANISM: Artificial Sequence
<220> FEATURE:
<223> OTHER INFORMATION: primer

<400> SEQUENCE: 34
cttttcctat cacaaaaata atccg                                              25
```